United States Patent [19]
Corn

[11] Patent Number: 5,385,139
[45] Date of Patent: Jan. 31, 1995

[54] METHOD AND APPARATUS FOR TESTING ANETHESIA MACHINE VALVES

[76] Inventor: Stephen B. Corn, 566 Commonwealth Ave., Apt. 1009, Boston, Mass. 02215

[21] Appl. No.: 66,719

[22] Filed: May 24, 1993

[51] Int. Cl.6 .................................... G01M 3/02
[52] U.S. Cl. ...................... 128/200.24; 128/202.22; 73/40
[58] Field of Search ............ 128/200.24, 202.22, 128/201.23, 205.13, 205.18; 73/37, 40, 40.7; 434/226, 270; 137/901

[56] References Cited

U.S. PATENT DOCUMENTS

| | | | |
|---|---|---|---|
| 2,399,643 | 5/1946 | Kreiselman | 128/29 |
| 3,808,706 | 5/1974 | Mosley et al. | 35/17 |
| 4,212,297 | 7/1980 | Johnson, Jr. et al. | 128/207 |
| 4,253,328 | 3/1981 | Pasternack | 73/40.7 |
| 4,344,144 | 8/1982 | Damico | 364/510 |
| 4,430,893 | 2/1984 | Barkalow | 73/168 |
| 4,796,467 | 1/1989 | Burt et al. | 128/202 |
| 4,870,962 | 10/1989 | Sitnik | 128/205.13 |
| 4,903,529 | 2/1990 | Hodge | 73/168 |
| 4,996,980 | 3/1991 | Frankenberger et al. | 128/200 |
| 5,048,329 | 9/1991 | Marchini | 73/168 |
| 5,057,822 | 10/1991 | Hoffman | 340/611 |
| 5,176,153 | 1/1993 | Eberhardt | 128/897 |
| 5,222,491 | 6/1993 | Thomas | 128/205.13 |

FOREIGN PATENT DOCUMENTS

| | | | |
|---|---|---|---|
| 4129848 | 3/1993 | Germany | 128/202.22 |
| 399657 | 3/1965 | Switzerland | 128/205.18 |

OTHER PUBLICATIONS

Hospital Accessories Catalog 1992, "Tests Lungs and Stoppers".

Primary Examiner—Edgar S. Burr
Assistant Examiner—Eric P. Raciti
Attorney, Agent, or Firm—Thomas J. Engellenner; William C. Geary, III

[57] ABSTRACT

A method and apparatus for testing flow control valves is disclosed. Specifically, the flow control valves of anesthesia machines are tested. The method contemplates the application of positive and negative air pressure to the valve being tested. If the valve is functioning properly, the valve will open or seal as expected. An apparatus is disclosed which enables a technician to apply either negative or positive pressure to the flow control valve and determine whether the valve is opening and sealing properly. The apparatus includes a pump for creating the air pressure and a fitting adapted to sealingly engage the port of the valve. The apparatus is simple to use and reduces the risk of transmitting disease.

22 Claims, 3 Drawing Sheets

METHOD AND APPARATUS FOR TESTING ANETHESIA MACHINE VALVES

BACKGROUND OF THE INVENTION

This invention relates to a method and apparatus for testing flow control valves and more particularly, the testing of the flow control valves of an anesthesia delivery apparatus.

The vast majority of hospitals, clinics and other health care institutions utilize gas anesthesia in administering health care to their patients. The preferred method is to utilize an anesthesia machine to control the flow of these gases to and from the patient. Because a patient's life may depend upon the proper administration of anesthesia, it is critical that the health care provider ensure that an anesthesia machine is functioning correctly.

A gas anesthesia machine is an extremely complex piece of equipment. It regulates the flow of anesthesia gases, typically $O_2$ and $N_2O$. It controls the mixture of these gases and an anesthetic agent as well as the removal of $CO_2$ from the gases as they flow through the system.

The gas anesthesia machine may be broken down into several systems, each performing a specific function. The control system consists of a complex system of valves, regulators, vaporizers and manifolds which precisely control the mixture of the gases and anesthesia agents and the pressure at which this mixture is provided at the machine or common gas outlet port. The patient system or circuit consists of an absorber, inhalation and exhalation check valves, a pressure limiting valve and a corrugated breath circuit attached to a mask for controlling the delivery of anesthesia to the patient.

In a typical rebreathing system, the absorber may contain one or more canisters of absorbent granules for removing $CO_2$ from the gas. The input to the absorber is connected through a pressure limiting valve and rebreathing bag to the exhalation check valve and the exhalation port. The output of the absorber is connected to the inhalation check valve and the inhalation port. In a non-rebreathing system, an absorber is not used and the anesthetic gas is delivered directly from the control system to the patient.

The inhalation and exhalation check valves control the flow of anesthesia gas to and from the patient. When a patient inhales, the inhalation check valve opens to permit the free flow of essentially $CO_2$-free anesthesia gas to the patient. At the same time, the exhalation check valve closes, preventing previously exhaled gases from being inhaled. When the patient exhales, the exhalation check valve opens and directs the flow of exhaled gases into the absorber for $CO_2$ absorption. At the same time, the inhalation check valve closes preventing the mixture of anesthesia and exhaled gases.

As can be seen, if either or both these valves fail to function properly, there is a potential for serious injury to the patient. Therefore, it is extremely important that these valves be tested on a regular basis.

The current method for testing the valves requires an anesthetist to place the mask of the patient circuit over his or her own nose and mouth to breath into the system. Individual valves are tested by inhaling and exhaling into each port. Visual observation and feel enable the anesthetist to verify the functionality of the check valves. This method is unacceptable because it increases the risk of transmitting communicable diseases, including AIDS and hepatitis. Indeed, many clinicians do not perform this very important machine valve test, fearing exposure of communicable diseases from the anesthesia machine.

The present invention provides a method and apparatus for testing the functionality of inhalation and exhalation check valves which virtually eliminates the risk of transmitting disease. The present invention includes a relatively simple and inexpensive apparatus for manually creating an artificial source of positive and negative gas pressure. The application of positive and negative gas pressure to the inhalation and exhalation check valves permits an anesthetist to verify their functionality without exposing himself/herself or a patient to the increased risk of disease.

Accordingly, it is one object of the present invention to provide an improved method and apparatus for testing flow control valves.

Another object of the present invention is to provide an improved method and apparatus for testing check valves in an anesthesia machine.

It is another object of the present invention to provide an improved method and apparatus for testing check valves in an anesthesia machine that provides for the reduced risk of transmitting disease to the patient and the anesthetist.

It is a further object of the present invention to provide an improved apparatus for testing check valves in an anesthesia machine that is inexpensive to produce and simple to use.

Other objects will be apparent from the disclosure which follows.

SUMMARY OF THE INVENTION

A method and apparatus are disclosed for testing the valves of an anesthesia machine. The apparatus employs a manually operable pump or pumping device as a source of air pressure. The pump is attached to the anesthesia machine via a special fitting specifically adapted to provide an air tight seal with the inhalation or exhalation ports of a gas anesthesia machine.

The pump may be self restoring in that it is able to expand to its original volume prior to being compressed. Once the pump creates a source of positive pressure and upon release, the pump creates a source of negative pressure. Alternatively, the pump may be manually expanded by the use of handles.

By attaching the pump to the exhalation port of the anesthesia machine and compressing the pump, positive pressure is applied to the exhalation valve. If the valve is functioning properly, the pump should compress easily. The pump is then expanded, either manually or automatically, and negative pressure is applied to the exhalation valve when the valve is functioning properly, it will close and seal the port, and the pump should be unable to restore itself. Conversely, when the valve is defective (e.g. leaking), this would be manifest by the pump's ability to restore itself.

The inhalation port is tested in an analogous manner. The pump is attached to the inhalation port in its compressed state and released. The pump's ability to be expanded, indicates that the valve is opening properly. The pump is then compressed and positive pressure is applied to the inhalation port. If the valve is functioning properly, the valve should close and resist compression of the pump. If the valve were not closing completely or otherwise leaking, this would be reflected by the pump's ability to become compressed.

The invention will next be described in connection with certain illustrated embodiments; however, it should be clear that various changes, additions and subtractions can be made without departing from the spirit and scope of the invention. In particular, it should be appreciated the that pump may take many forms and a hose or other fluid connecting means may or may not be used to connect the pump with the fitting.

BRIEF DESCRIPTION OF THE DRAWINGS

A more complete understanding of the invention may be obtained by reference to the drawings in which.

DETAILED DESCRIPTION

Figure 1:
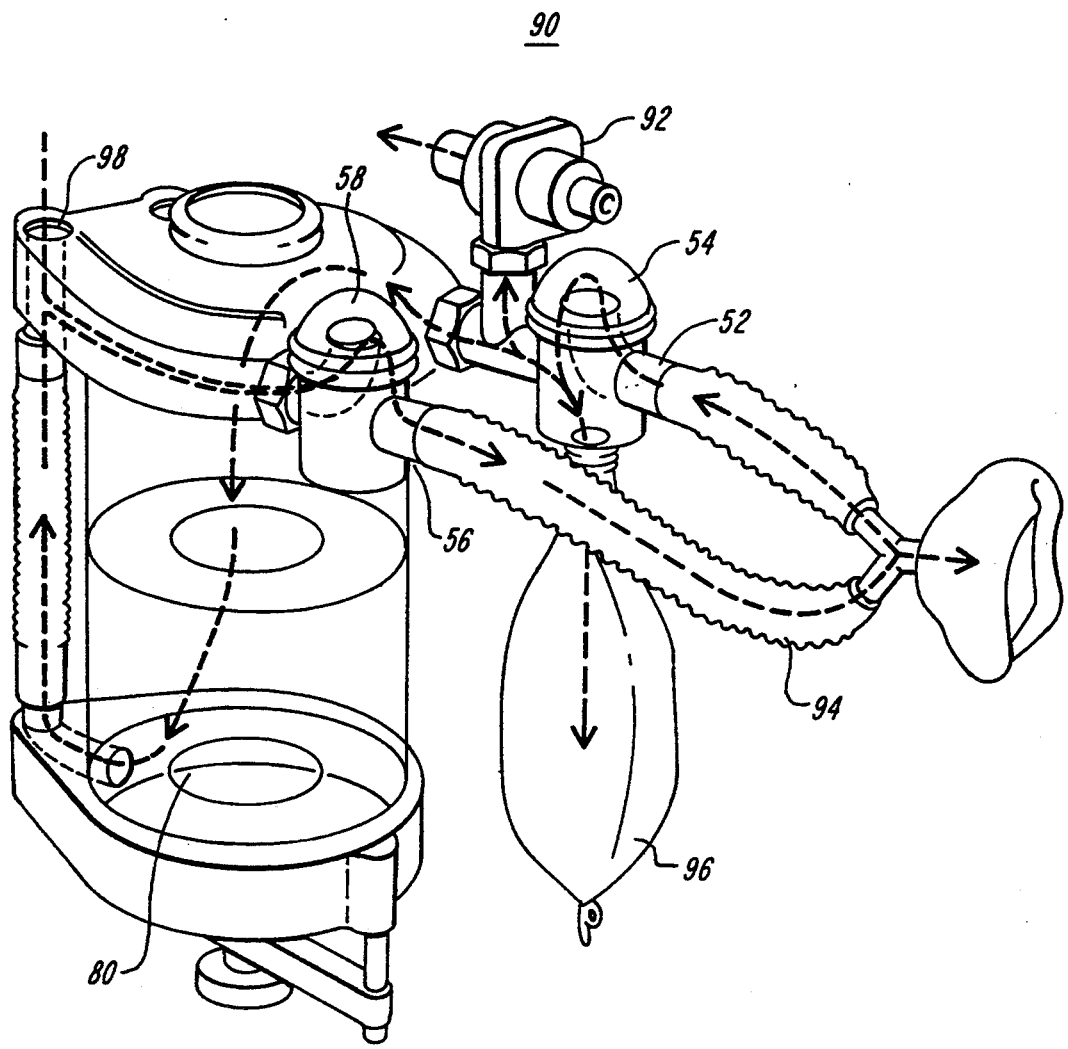
FIG. 1 is an illustration of the patient circuit of a representative anesthesia machine.

FIG. 1 illustrates a typical patient system of an anesthesia machine. The system 90 includes an absorber canister 80 which absorbs $CO_2$ from the air as it flows through the system. The patient breathing circuit 94 includes a mask and two segments of corrugated breath tubes. One segment is attached to the exhalation port 52 and the other is attached to the inhalation port 56. During inhalation, the inhalation valve opens and anesthesia gas is drawn from fresh gas inlet 98 as well as from the absorber canister 80. During exhalation, the exhalation valve opens and exhaust air is forced into rebreathing bag 96 and absorber canister 80. If the combined pressure of exhalation, the air in the expanded rebreathing bag 96 and the incoming fresh gas 98 is greater than a preset limit, the pressure limiting valve 92 opens to release excess pressure.

Figure 2A:
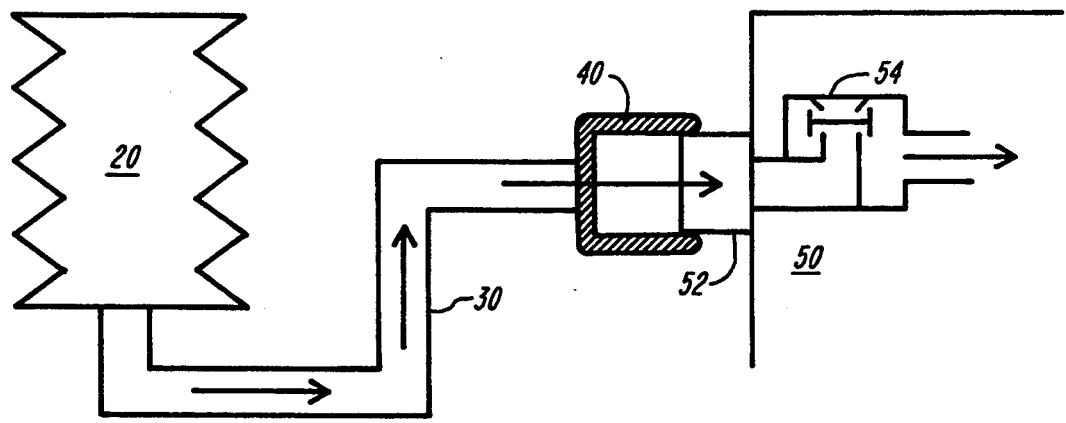
FIGS. 2A and 2B are diagrammatic illustrations of the apparatus in accordance with the present invention in the expanded (FIG. 2A) and compressed (FIG. 2B) conditions.
Figure 2B:
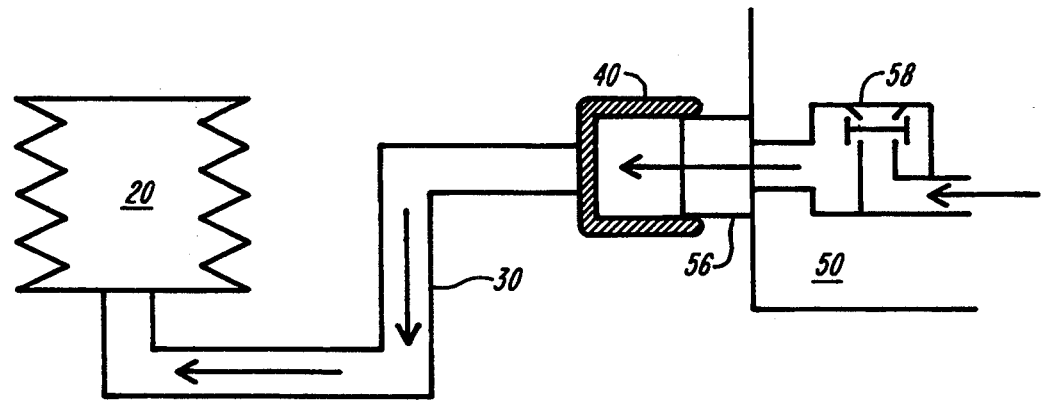

FIGS. 2A and 2B are diagrammatic views of the apparatus of a preferred embodiment of the invention. The valve testing device includes a pump 20, a hose 30 and a fitting 40. The pump 20 is a self-restoring bellows which may return to substantially its original volume after being compressed. The hose 30 comprises a flexible tubing which connects the pump 20 to the fitting 40). The hose 20 may Be molded integrally with the pump 20 or may be adapted to mate and form an airtight seal with a portion of the pump 20.

The fitting 40 is designed and adapted to form an air-tight seal with the inhalation port 56 or exhalation port 52 of an anesthesia machine 50. The fitting 40 has a cylindrical portion with a substantially smooth interior surface able to slide over a cylindrical portion of inhalation port 56 or exhalation port 52. The interior diameter of the fitting 40 is substantially the same diameter as the outside diameter of the cylindrical portion of the ports 52, 56. When the fitting 40 is attached to one of the ports, the interior surface of the fitting 40 is in sealing contact with the exterior surface of the port, thus forming an air tight seal.

The fitting 40 may be molded integrally with the hose 30 or may be adapted to mate and form an air-tight seal with the hose 30. This provides an air-tight seal when the fitting 40 mates with inhalation port 56 or exhalation port 52. It should also be noted that the fitting 40 may be molded integrally with the pump 20 or likewise adapted to mate and form an air-tight seal with a portion of pump 20 without utilizing a hose of any kind.

As shown in FIG. 2A, the exhalation valve 54 is tested by removing the patient breathing circuit 94 and, with pump 20 in the expanded state, connecting the fitting 40 to the exhalation port 52. The pump 20 is then used to create a positive pressure at the fitting 40 and to force air into exhalation port 52. If the pump 20 cannot force air into the exhalation port 52, then the valve is defective. The pump is then released and allowed to expand thus creating a negative pressure at the fitting 40. If the pump 20 expands, then the valve is not sealing properly as no air should be allowed to be escape from the exhalation port.

As shown in FIG. 2B, the inhalation valve 58 is tested by removing the patient breathing circuit and connecting fitting 40 to the inhalation port 56 with pump 20 in the compressed state. The pump 20 is then expanded and a negative pressure is created at the fitting 40. The inability of the pump to expand indicates that valve 58 is defective. The pump 20 is then compressed and resistance is met. If the valve is sealing properly, the pump will compress very little. If the valve is leaking the pump will compress with little resistance.

The device of present invention permits the valves of an anesthesia machine to be tested in a relatively safe, quick and easy manner. The risk of transmitting disease is reduced because an anesthetist does not breathe into the mask of the patient breathing circuit. Further, the device is relatively inexpensive to produce and may be disposed of after one use.

The pump 20, hose 30 and fitting 40 may be formed from conventional plastics, and the dimensions of these components can be determined by one of ordinary skill in the art. Preferably, however, the length of the hose is approximately 3 inches, and the hose may be made from corrugated tubing or rigid, smooth tubing. The hose 30 may, of course, have a length greater or less than 3 inches as necessary to meet the needs of a given application. In a preferred embodiment, the fitting 40 has an inside diameter of 22 mm. The fitting 40 may also include threads and a seal which mate with corresponding threads on the anesthesia machine to form an air tight seal. Fitting 40 may also include a tapered portion to enhance its sealing ability.

Figure 3A:
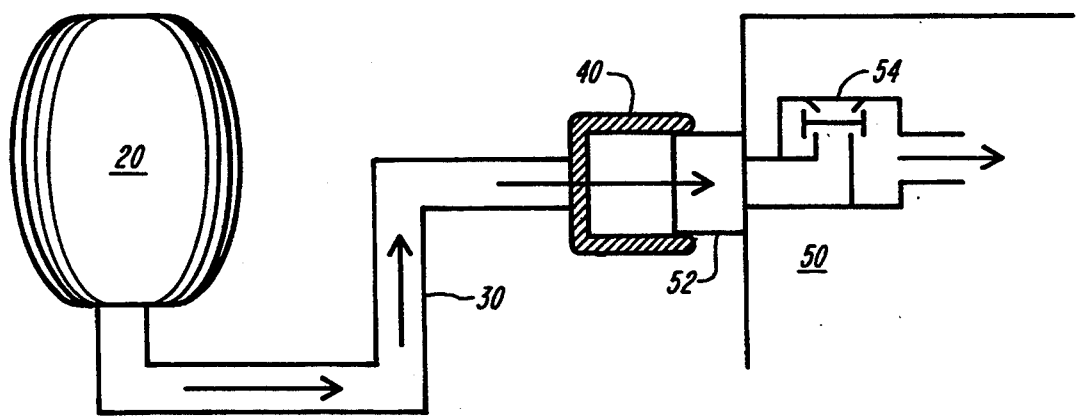
FIGS. 3A and 3B illustrate one alternative embodiment of the pump of the present invention.
Figure 3B:
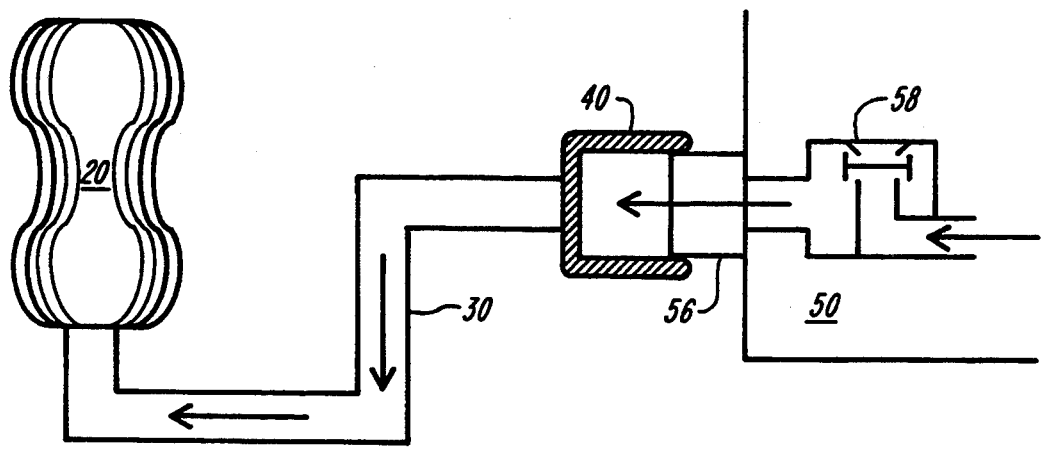

FIGS. 3A and 3B show an alternative embodiment of the present invention wherein the pump 20 comprises a squeeze bulb. The squeeze bulb pump 20 is self restoring such that after being compressed, as shown in FIG. 3B, it is able to return to its original volume as shown in FIG. 3A. The squeeze bulb pump 20 may be molded of conventional plastics or rubbers. The hose 30 may be integral with the pump 20 or separately attached in any known manner that forms an air-tight seal. The fitting 40 may also be integrally formed with the hose or separately attached. In addition, the fitting 40 may be directly attached to the pump 20 without the intermediate hose.

Figure 4:
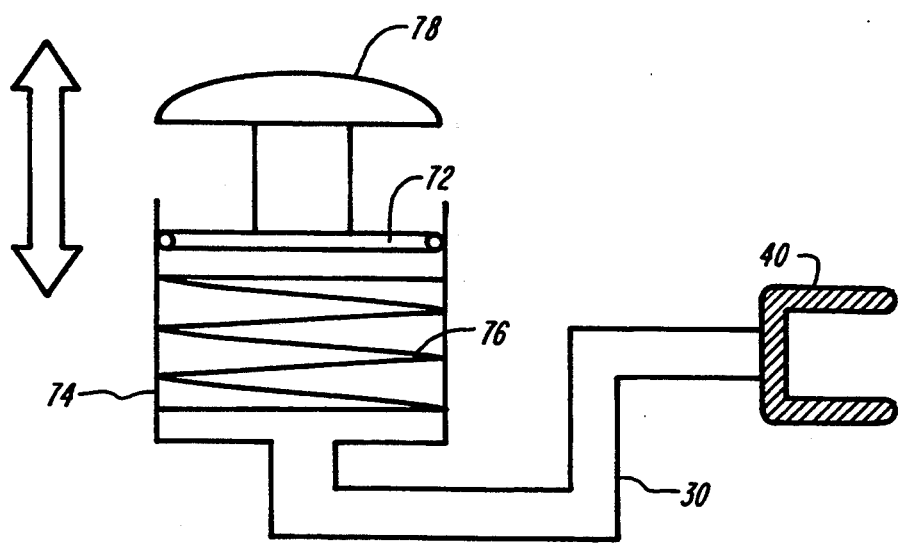
FIG. 4 illustrates another alternative embodiment of the pump of the present invention.

FIG. 4 shows another embodiment of the present invention wherein the pump 20 comprises a piston 72 and cylinder 74. When the handle 78 is pressed into the cylinder 74, the pump 20 creates a positive pressure at the fitting 40. When the handle 78 is pulled out of the cylinder 74, the pump 20 creates a negative pressure at the fitting 40. A spring 76 may be provided to permit the piston to automatically return to its expanded position and at the same time create negative pressure at the fitting.

The device shown in FIG. 4 may be utilized in a slightly different method than the embodiments described above. In the embodiments of FIGS. 2A, 2B, 3A, 3B, the negative pressure is limited by the restoring force inherent in the material. The device of FIG. 4 may be used where a greater negative pressure is necessary. Negative pressure at the fitting 40 may be increased by using the handle 78 to pull the piston out of the cylinder 74.

It will be apparent to one of ordinary skill in the art that the different features disclosed may be utilized in other embodiments. For example, it may be desirable to provide the embodiment of FIGS. 2A and 2B with handles at each end to permit a larger negative pressure to be created. It may also be advantageous to provide in the pump of FIGS. 2A and 2B a restoring spring like that shown in FIG. 4 to increase the negative pressure produced. Other modifications will be obvious and should not be considered to be beyond the scope of the invention.

The invention may be embodied in other specific forms without departing from the spirit or essential characteristics thereof. The present embodiments are therefore to be considered in respects as illustrative and not restrictive, the scope of the invention being indicated by the appended claims rather than by the foregoing description, and all changes which come within the meaning and range of the equivalency of the claims are therefore intended to be embraced therein.

What is claimed is:

1. Apparatus for testing the valves of an anesthesia machine said valves having respective ports comprising
   pump means for generating a source of positive and negative gas pressure; and
   connection means for individually and selectively connecting said pump means to said respective port of at least one valve of an anesthesia machine in order to evaluate the opening and closure of said valve in response to the pressure exerted by the pump means.

2. The apparatus according to claim 1 further comprising
   tube means for operatively connecting said pump means to said connections means.

3. The apparatus according to claim 1 wherein
   the connection means comprises a connector having a 22 millimeter inside diameter.

4. The apparatus according to claim 1 wherein
   said pump means is expandable to an expanded position and creates negative pressure at said connection means.

5. The apparatus according to claim 4 wherein
   said pump means further includes restoring means for restoring said pump means to a compressed position from said expanded position.

6. The apparatus according to claim 1 wherein
   said pump means is compressible to a compressed position and creates positive pressure at said connection means.

7. The apparatus according to claim 6 wherein
   said pump means includes restoring means for restoring said pump means to an expanded position from said compressed position.

8. The apparatus according to claim 1 wherein
   said pump means further comprises an expandable and compressible bellows.

9. The apparatus according to claim 8 wherein
   said bellows includes restoring means for restoring said bellows to an expanded position from a compressed position.

10. The apparatus according to claim 1 wherein
    said pump means comprises an expandable and compressible squeeze bulb.

11. The apparatus according to claim 10 wherein
    said squeeze bulb includes restoring means for restoring said squeeze bulb to an expanded position from a compressed position.

12. The apparatus according to claim 1 wherein
    said pump means comprises an expandable and compressible cylinder having piston.

13. The apparatus according to claim 12 wherein
    said cylinder includes a handle means for moving said piston and expanding and compressing said cylinder.

14. The apparatus according to claim 12 wherein
    said cylinder includes restoring means for restoring said cylinder to an expanded position from a compressed position.

15. A method of testing an exhalation valve of an anesthesia machine comprising the steps of:
    individually and selectively connecting a pump means to provide a source of gas pressure to a port of said valve,
    applying a positive gas pressure to said port,
    verifying said positive pressure is passed through said valve,
    applying a negative gas pressure to said port,
    verifying said negative pressure is not passed through said valve.

16. The method according to claim 15 wherein said step of applying a positive gas pressure to said port includes compressing a pump means for creating gas pressure.

17. The method according to claim 15 wherein said step of applying a negative gas pressure to said port includes expanding a pump means for creating gas pressure.

18. The method according to claim 17 wherein a restoring means expands said pump means.

19. A method of testing an inhalation valve of an anesthesia machine comprising the steps of:
    individually and selectively connecting a pump means to provide a source of gas pressure to a port of said valve,
    applying a negative gas pressure to said port,
    verifying said negative pressure is passed through said valve,
    applying a positive gas pressure to said port, and
    verifying said positive pressure is not passed through said valve.

20. The method according to claim 19 wherein
    said step of applying a positive gas pressure to said port includes compressing a pump means for creating gas pressure.

21. The method according to claim 19 wherein
    said step of applying a negative gas pressure to said port includes expanding a pump means for creating gas pressure.

22. The method according to claim 21 wherein
    a restoring means expands said pump means.

* * * * *